United States Patent [19]

Takagi et al.

[11] Patent Number: 5,166,985
[45] Date of Patent: Nov. 24, 1992

[54] METHOD AND APPARATUS FOR INSPECTING SURFACE PATTERN OF OBJECT

[75] Inventors: Yuji Takagi, Yokohama; Seiji Hata, Fujisawa, both of Japan

[73] Assignee: Hitachi, Ltd., Tokyo, Japan

[21] Appl. No.: 686,352

[22] Filed: Apr. 17, 1991

[30] Foreign Application Priority Data

Apr. 18, 1990 [JP] Japan .................................. 2-100294

[51] Int. Cl.⁵ .............................................. G06K 9/00
[52] U.S. Cl. ........................................ 382/8; 358/106; 356/237
[58] Field of Search ...................... 382/8, 17; 356/237; 358/101, 106, 107

[56] References Cited

U.S. PATENT DOCUMENTS

| | | | |
|---|---|---|---|
| 4,677,473 | 6/1987 | Okamoto et al. | 358/101 |
| 4,692,690 | 9/1987 | Hara et al. | 358/106 |
| 4,740,079 | 4/1988 | Koizumi et al. | 356/237 |
| 4,988,202 | 1/1991 | Nayar et al. | 358/101 |

Primary Examiner—Leo H. Boudreau
Assistant Examiner—David Fox
Attorney, Agent, or Firm—Antonelli, Terry, Stout & Kraus

[57] ABSTRACT

A method and an apparatus for inspecting a three-dimensional surface shape and pattern of an object under inspection by images of the surface of the object, said images being formed by reflected light rays from the object illuminated by lights. The surface of the object is illuminated by first and second lights provided on the inspected surface side of the object and at different heights from the object, images of the reflected light rays from the surface of the object illuminated by the first and second lights are acquired by an imaging unit, a first image of the surface of the object illuminated by the first light and a second image of the surface of the object illuminated by the second light, both acquired by the imaging unit, are input separately, brightness values at the same pixel points of the first and the second images are subjected to a division process to obtain a value, and by using this value as the brightness value of the pixel, a third image is formed which is used for quality evaluation.

18 Claims, 9 Drawing Sheets

METHOD AND APPARATUS FOR INSPECTING SURFACE PATTERN OF OBJECT

BACKGROUND OF THE INVENTION

This invention relates to a method and an apparatus for inspecting a surface shape and pattern of an object, and more particularly to a method and an apparatus for inspecting a three-dimensional shape and pattern of the surface of an object.

As examples of an apparatus for inspecting a three-dimensional shape and pattern of the surface of an object, apparatuses for inspecting the soldered condition of an electronic part after the electronic part has been mounted on a board are described in JP-A-61-293657 (literature (1)), and "A Tiered-Color Illumination Approach for Machine Inspection of Solder Joints", David W. Capson and Sai-Kit Eng, IEEE Transactions on Pattern Analysis and Machine Intelligence, Vol 10, No. 3, May 1988, pp. 387-393 (literature (2)).

In the literature (1), a solder joint under inspection is illuminated sequentially from a plurality of angles, the features such as shapes of highlight produced by regular reflection of illumination are extracted in binary form from the images obtained by illumination from the different angles, and the solder joint is judged as to whether or not it is acceptable from a total assessment of the features obtained from the respective images. To switch over illumination from the plurality of angles, a shutter mechanism is used or monochrome LEDs which can be switched at high speed are used.

In literature (2), the solder joint is illuminated by two high-angle and low-angle lights of different emission frequencies, and from images obtained by illumination from different angles, the solder joint is judged whether it is acceptable or not.

SUMMARY OF THE INVENTION

However, in any of the prior art techniques mentioned above, no consideration is given to the diversity of the luster condition of the solder surface. Specifically, the solder surface may be like a mirror surface or frosty depending on the kind of solder even just after the soldering is finished. Generally, even the solder joint with a mirror-like surface will have a frosty appearance with passage of time. In the manufacturing process of printed circuit boards (PCB), substances, such as flux, which can be the cause of contamination on the solder surface. Therefore, it is difficult to uniquely decide an optimal binary threshold to optimally extract the soldered condition from solder images acquired under fixed illumination.

In other words, when the solder surface becomes frosty or stained, the reflectance of illumination from the lights to the camera is reduced, and therefore, the intensity of even a regular-reflection light decreases. As a result, the surface shape of the solder joint cannot be detected accurately.

For this reason, it is necessary to adjust a binary threshold for binary digitization of images from the camera owing to differences in the soldering process, the PCB manufacturing process and the kind of solder. The turn-on and turn-off operations of the lights, which are turned on and turned off a great number of times to control the illumination, affect the service life of the shutter mechanism. The monochrome LED is superior in the high-speed switching performance and the service life, and suitable for the solder joint inspection. In inspection of electronic parts, polarity markers, etc. other than the solder joint inspection, there is a possibility that the inspection is difficult owing to the relation between the wavelengths of the marker color and the source of illumination.

This invention has been made to solve the above-mentioned problems of the prior art techniques, and has as its object to provide a method and an apparatus capable of inspecting the three-dimensional shape and pattern of the surface of an object in a stable and simple manner regardless of the surface condition of the object.

According to an aspect of this invention, to achieve the above object, there is provided an apparatus for inspecting the surface shape and pattern of an object, which comprises first and second lighting units, provided on the inspected surface side of an object and at different heights from the object, for illuminating the surface of the object; an imaging unit for acquiring an image of lights reflected from the surface of the object illuminated by the first and second lighting units; an input unit for accepting a first image of the surface of the object illuminated by the first lighting unit and a second image of the surface of the object illuminated by the second lighting unit; and a unit for performing a division process between brightness values at the same pixel points of the first and second images accepted by the input unit and forming a third image by using a value derived from said division process as the brightness value at the pixel.

In this invention, multiple, for example, two lights are provided at different heights from the object being inspected and on the surface side of the solder joint of the object on a circuit board.

Under the above-mentioned arrangement, the flat area of the solder joint illuminated by the upper light reflects back lots of regular-reflection light and the inclined area of the solder joint illuminated by the lower light reflects back lots of regular-reflection light. By performing a division process between the brightness values at the same pixels of the images by the upper and lower lights, a ratio of reflection of illumination by the upper and lower lights can be obtained. From this ratio, how much the solder surface is inclined can be known. Since the intensity of the reflected light is not used and since the ratio is used, the degree of the inclination of the solder surface can be evaluated regardless of the variation of the reflecting condition of the solder surface. Therefore, the presence or absence of solder, insufficient solder, solder bridge, etc. can be detected with high reliability.

When lamps with different wavelengths of light are used, an illumination arrangement can be obtained which has a wide range of wavelengths close to natural light. This makes it possible to clearly observe electronic parts, polarity markers, etc., for example, other than the solder joints.

Thus, automatic inspection of solder joints can be realized. By using an optical system according to this invention, polarity markers, etc. can be inspected.

DESCRIPTION OF THE PREFERRED EMBODIMENTS

Preferred embodiments of this invention will be described in detail with reference to the accompanying drawings. In the drawings, the same reference numerals designate the parts having the same functions.

As a preferred embodiment of this invention, description is made of an apparatus embodying this invention for automatically inspecting the soldered condition of electronic parts after they have been mounted on a PCB.

Figure 1:
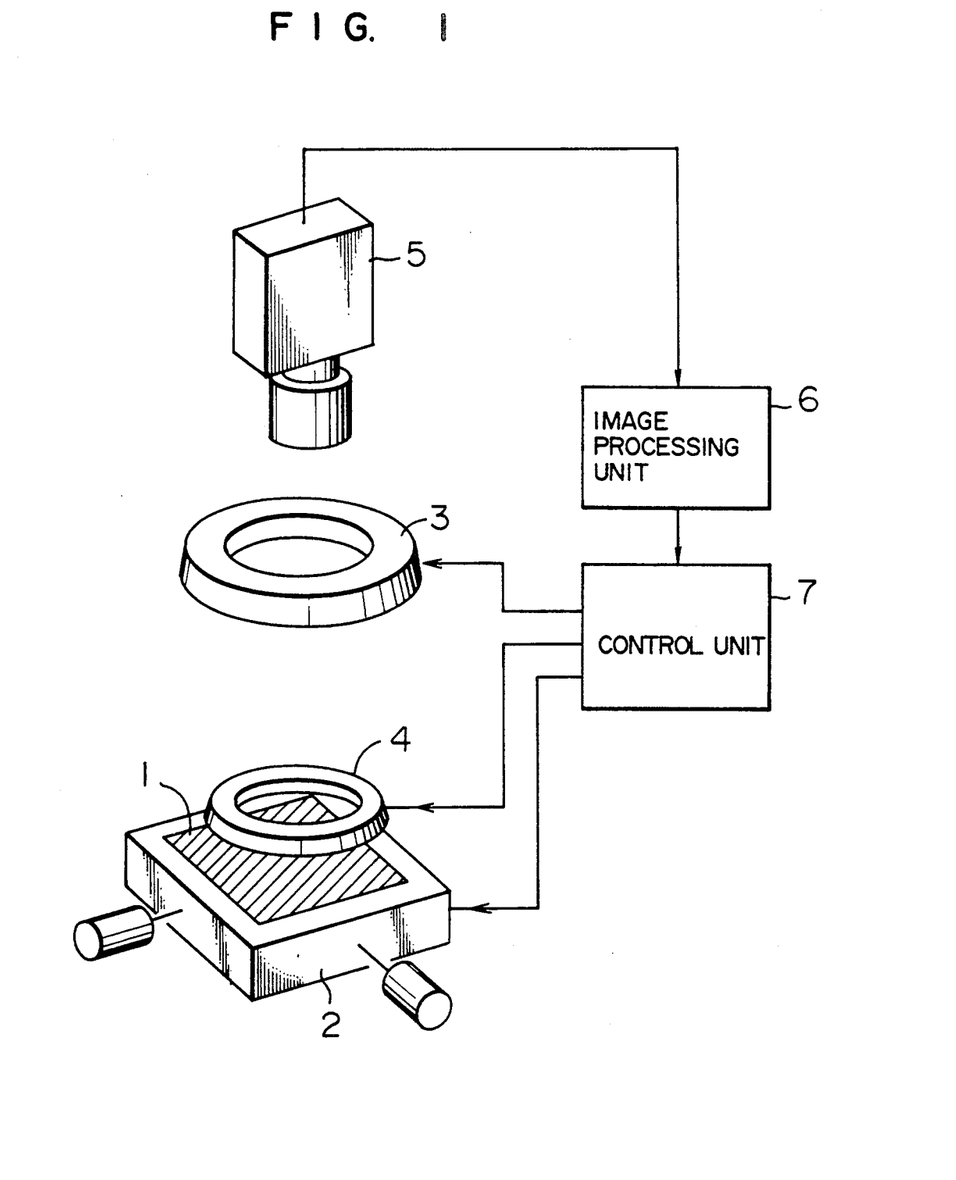
FIG. 1 is a diagram showing a whole arrangement as an embodiment of an apparatus for inspecting the soldered condition of electronic parts according to this invention.

FIG. 1 shows an arrangement of a soldered condition inspection apparatus embodying this invention as described. Reference numeral 1 indicates a PCB under inspection which has electronic parts mounted and soldered thereto. The PCB under inspection is placed on an X-Y table and is moved according to an inspection sequence to be described later. Lights 3, 4 are used to illuminate the PCB 1. For example, circular lights are mounted coaxially at upper and lower positions as shown in FIG. 1. Reference numeral 5 indicates an imaging device such as a TV camera using a CCD (charge-coupled device), and the imaging device detects an optical image of that inspected part of the PCB which is illuminated by the lights 3, 4, and inputs an acquired video signal into an image processing unit 6. The position control of the X-Y table 2 and the ON-/OFF control of the lighting units 3, 4 are performed by a controller 7.

Figure 2A:
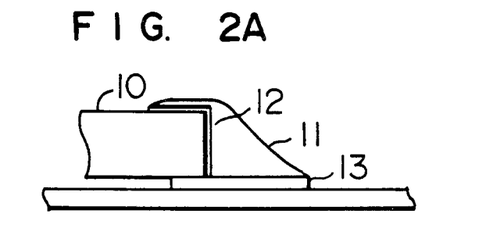
FIG. 2A is a sectional view of an example of a solder joint as an object of inspection.
Figure 2B:
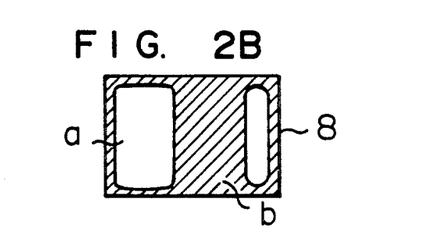
FIGS. 2B, 2C show examples of images obtained by illuminating a solder joint of the inspected object with upper and lower lights 3, 4.
Figure 2C:
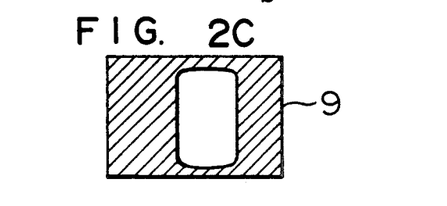

FIGS. 2B, 2C show images obtained by illuminating the solder joint inspection of the PCB with the upper and lower lights 3, 4. FIG. 2A is a sectional view of the solder joint under inspection. In the sectional view of FIG. 2A, reference numeral 10 indicates an electronic part, 11 the solder, 12 an electrode of the electronic part, and 13 a soldering pad on the board. Images are acquired as a train of electrical pulses representing the light intensities. However, for the sake of simplicity, in FIGS. 2B, 2C, in the solder joint, the white areas a indicate the brightly illuminated areas by lighting, while the hatched areas b indicate the relatively dark areas. It is understood from FIGS. 2B, 2C that the way of reflection of light varies between the upper light 3 or the lower light 4. This is because the solder surface inclination at which a regular reflection of illumination occurs differs between the upper and lower lights. More specifically, as is clear from the side view in FIG. 3A of the optical system (3, 4, 5) of FIG. 1, when the solder joint is illuminated by the upper light 3, the reflected light rays are stronger if the solder surface is flat, and when the solder joint is illuminated by the lower light 4, the reflected light rays are stronger if the solder surface is inclined. The installed position of the upper and lower lights 3, 4 can be selected arbitrarily. However, due to the conditions shown in FIG. 3A, as the illumination light from the upper light 3 becomes closer to vertical and as the illumination light from the lower light 4 becomes closer to horizontal, images change greatly by different inclinations of the solder surface.

Figure 3A:
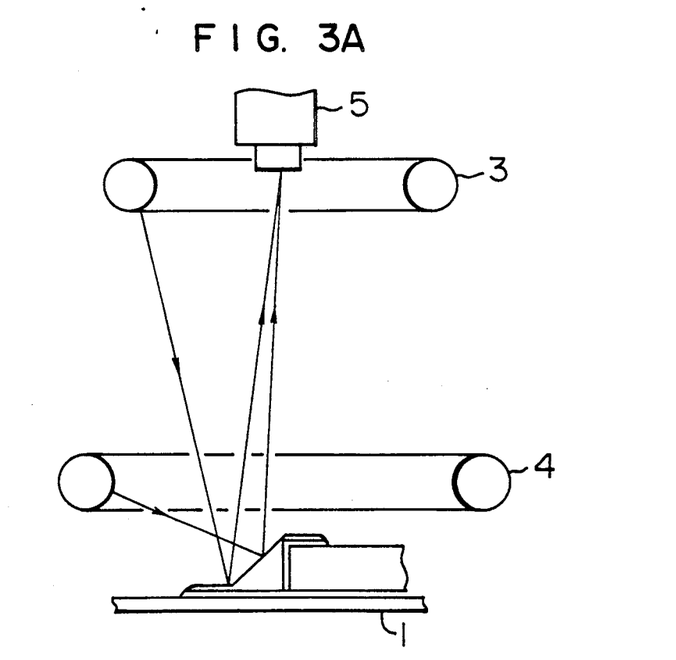
FIG. 3A is a diagram showing the relation between positions of the lights of the optical system of FIG. 1 and the reflected light from the solder joint to a camera.
Figure 3B:
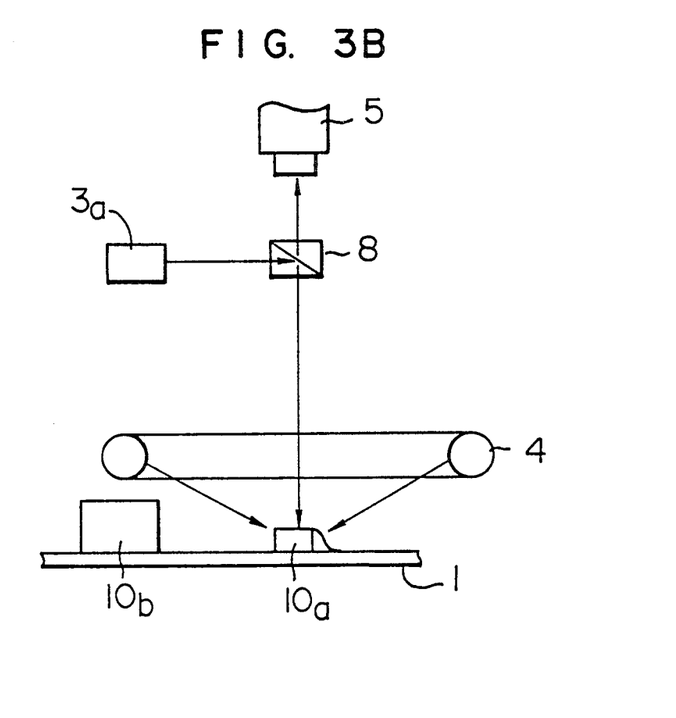
FIG. 3B is a side view of a modification of the optical system used in the embodiment of FIG. 1.

As a countermeasure, as shown in FIG. 3B, in place of the ring light 3, it is possible to provide a half mirror or a cube beam splitter 8 right below the camera 5 at the same height as the position of the light 3, and also, a spot light 3a for emitting a spot beam parallel with the board 1 to emit a light beam from right above a part 10a being inspected. The lower light 4 is disposed at a height where the light 4 will not come into contact with another part 10b on the board 1.

It is also possible to obtain the geometric features of highlights by regular-reflection light beams in the form of binary data, for example, by using two images shown in FIG. 2 and make a accept-reject decision on the solder joint by a total examination of the features acquired from those images. In view of a variety of the luster condition of the solder surface and the contamination of the solder surface by flux in the manufacturing process of PCBs, it is considered likely that there will be some effects on the reliability of inspection if an optimum binary threshold is decided uniquely to optimally extract the solder condition from solder-joint images captured under illumination of the fixed lights. To avoid this problem, this invention uses a method of dividing data on an image 8 by the upper light in FIG. 2B by data on an image 9 by the lower light in FIG. 2C. Let coordinates in an image be (I, J); let the brightness value of a pixel point (I, J) in an image 8 by the upper light be UPIC(I,J); and let the brightness value of a pixel point (I, J) in an image 9 by the lower light be DPIC(I,J). Suppose that the brightness is expressed in 256 stages. If UPIC(I,J) is larger than DPIC(I,J), an image value DVDPIC(I,J) obtained by division as described is $$DVDPIC(I,J) = 128 + [\{UPIC(I,J)/DPIC(I,J)\} - 1] \times C \qquad (1)$$

If UPIC(I,J) is smaller than DPIC(I,J), $$DVDPIC(I,J) = 128 - [\{DPIC(I,J)/UPIC(I,J)\} - 1] \times C \quad (2)$$

Figure 4:
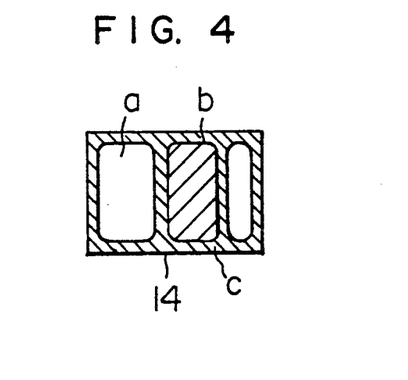
FIG. 4 is an example of image obtained by a division process between images of FIGS. 2B, 2C.

If the calculation result of DVDPIC(I,J) is less than 0, DVDPIC is made 0. And, if the calculation result is 256 or more, DVDPIC is made 255. In Eqs. (1) and (2), the constant C is any natural number. Supposing C is 30, if UPIC(I,J) is twice DPIC(I,J), that is, if the brightness value is twice higher for UPIC(I,J), DVDPIC is 158. In addition, if the brightness value is three times or four times higher, DVDPIC is 188 or 218. Conversely, if DPIC(I,J) is twice or three times higher than UPIC(I,J), DVDPIC(I,J) is 98 or 68. In other words, the constant C serves a kind of amplification factor in developing the ratio of UPIC(I,J) to DPIC(I,J) on the gray scale in expressing the gradation of brightness of the image. To be more specific, if the value of C is made large, a slight variation in the inclination can be displayed with the value of DVDPIC(I,J) centering round 128, but a conspicuously inclined area and a flat area of the solder joint are hard to be displayed. If the value of C is made small, an image of the inclined area with DVDPIC(I,J) of about 128 is rough. An image 14 of FIG. 4 is an example of result of processing two images of FIGS. 2B, 2C by Eqs. (1) and (2). In this case, the obtained values of the ratio are divided into three stages, for example, the area with the smallest ratio is expressed in white, the area with the intermediate ratio in gray, and the area with the largest ratio in black.

Specifically, the light (white) area corresponds to the flat area of the solder joint, and the dark (cross-hatched or black) area corresponds to the inclined area. The luminance of the intermediate (hatched or gray) area c indicates the intermediate area between the flat area and the inclined area. If the solder surface is completely like a mirror surface, the brightness of the solder surface excessively changes depending on whether or not there is a regular reflection of illumination from the upper and lower lights. Therefore, the values of DVDPIC obtained by Eqs. (1) and (2) will agglomerate in three groups: inordinately large or small or values close to 128. However, when the solder surface has some irregular-reflection components by its frosty or contaminated surface condition, even if the inclination of the solder surface is not in the condition of regular reflection, light rays are reflected also in the area surrounding the area so inclined as to cause regular reflection. The quantity of reflected light rays greatly changes according to the condition of the solder surface. Generally, the quantity of reflected light rays decreases still less as the inclination of the solder surface deviates from the angle at which regular reflection occurs. In this case, the values of DVDPIC obtained by Eqs. (1) and (2) spread in the range from 0 to 255. The larger the value of DVDPIC, that is, the brighter the image 14, the flatter the solder surface is. Conversely, the smaller the value of DVDPIC, that is, the darker the image 14, the more conspicuously inclined the solder surface is.

In this invention, a ratio of the quantities of reflected light at the same pixel is examined when an object being inspected is illuminated by two lights 3 and 4, and therefore, the degree of the inclination can be evaluated regardless of absolute quantities of reflected light, that is to say, regardless of the solder surface condition. In the following, brief description will be made of an example in which this invention is applied to inspection of solder joints of parts mounted on a PCB. A division-derived image obtained as a result of division process is a gray scale image in which the brightness varies continuously according to the ratio DVDPIC. A threshold process is performed to divide an image into areas corresponding to flat and inclined areas of a solder joint. As is clear from Eqs. (1) and (2), a pixel where a division-derived image value is larger than 128 can be considered to correspond to a flat area of the solder joint and a pixel where a division-derived image value is smaller than 128 will correspond to an inclined area of the solder joint. For the neighborhood of 128 where there is a transition region between the flat and inclined areas, an adequately selected margin M is provided for the transition region, the region is divided into a flat area of greater than (128+M) and an inclined area of smaller than (128−M), and the area from (128−M) to (128+M) may be neglected and may not be displayed. If such a division is made, when the solder joints of electronic parts mounted on a PCB shown in FIGS. 5A, 5B, 5C, 5E, and 5G are subjected to an accept-reject decision, their images are as shown in FIGS. 5B, 5D, 5F, and 5H. In FIGS. 5B, 5D, 5F, and 5H, the flat areas are expressed in white and the inclined areas are indicated by hatching. Incidentally, for gray-scale display, the values from above-mentioned divisions may be classified into three or more stages.

Figure 5A:
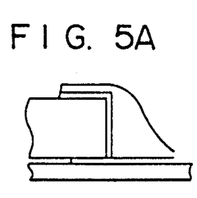
FIGS. 5A, 5C, 5E, 5G are side views showing soldered conditions of parts.
Figure 5B:
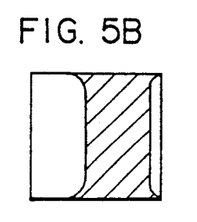
FIGS. 5B, 5D, 5F, 5H show images obtained by a division process between images of solder joints of FIGS. 5A, 5C, 5E, 5G.
Figure 5C:
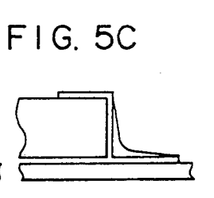
Figure 5D:
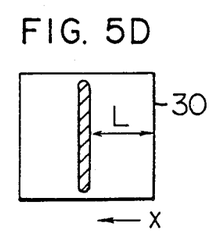
Figure 5E:
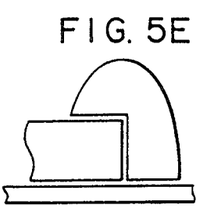
Figure 5F:
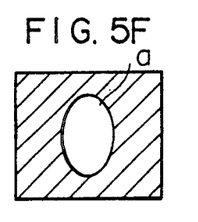
Figure 5G:
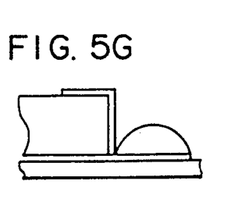
Figure 5H:
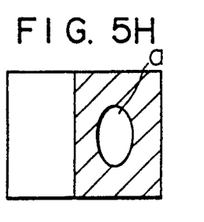

FIG. 5B shows a division-derived image of a normal condition of a solder joint. For soldering defects, such as no solder and insufficient solder, as shown in FIGS. 5C, 5D, a length L of the flat solder area from the end of the solder pad is measured along the center line of the solder joint, and when the length L is longer than a fixed value, this may be judged to be no solder or insufficient solder. In excess solder shown in FIGS. 5E, 5F or poor wetting due to insufficient solder in FIGS. 5G, 5H, the solder is laid in a convex form on the solder pad, and in a division-derived image, the area close to the top is flat and therefore, light and surrounded by the dark area, which is the inclined area. So, a check is made of the solder joint to see if there is an isolated segment as indicated by a in FIGS. 5E, 5H. If there is such a segment, you have only to judge if to what extent the segment a is surrounded by the dark area of the inclined area.

Figure 6A:
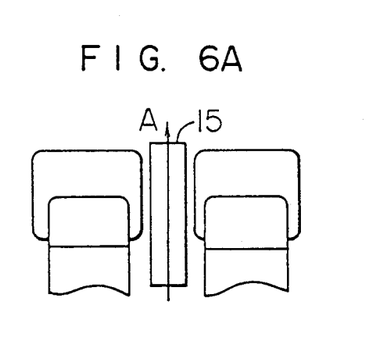
FIGS. 6A, 6C are plan views of solder joints with a bridge and with no bridge.
Figure 6B:
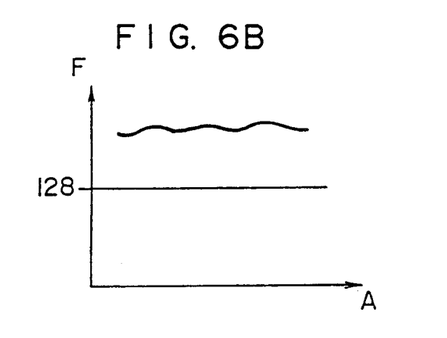
FIGS. 6B, 6D are diagrams showing the brightness in the directions of arrows A, A' in the images obtained by division processes in the windows of FIGS. 6A, 6C.

An example of a method of detecting a solder bridge will next be described. FIGS. 6a, 6B show plan views indicating a normal condition (no bridge) and an occurrence of a solder bridge which are observed through an inspection window 15 set at intermediate regions between electronic parts and also show images obtained as a result of a division process between images within the window. Graphs of FIGS. 6B, 6D show changes in brightness of division-derived images in the directions A and A' in the windows as shown above in the figures. The F of the graphs represents values of brightness. Normally, in division-derived images obtainable by this method, the circuit board surface or the like are picked up as a flat area. In other words, the reflected light rays from the circuit board are strong. Needless to say, the reflectance differs among the board surface, wiring pattern and printed characters, so that the values of DVDPIC in Eq. (1) for those areas differ. However, in any case, the reflected light rays by the upper light are stronger, so that it is evident that the values of DVDPIC are larger than 128. Even so, if a bridge is formed in such places mentioned above, the brightness at such a place fluctuates by the presence of solder, and therefore, the values of DVDPIC become less than 128 at the inclined areas on both sides of the bridge. As a result, if these changes are detected, it is possible to judge whether or not there is solder. FIGS. 6A, 6B schematically show the cases where a solder bridge is present and absent.

Figure 6C:
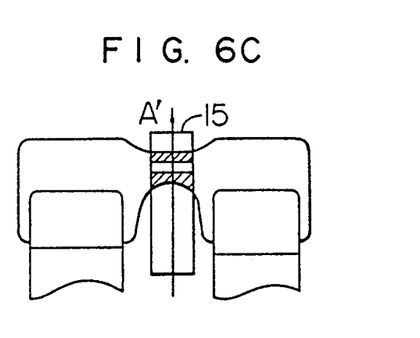
Figure 6D:
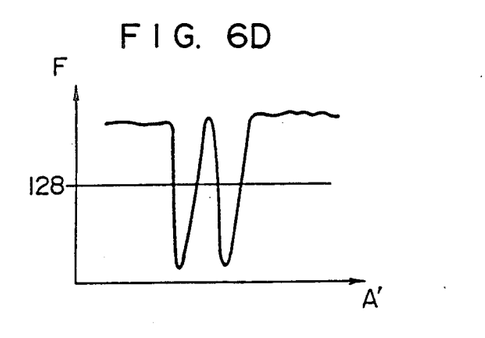
Figure 7:
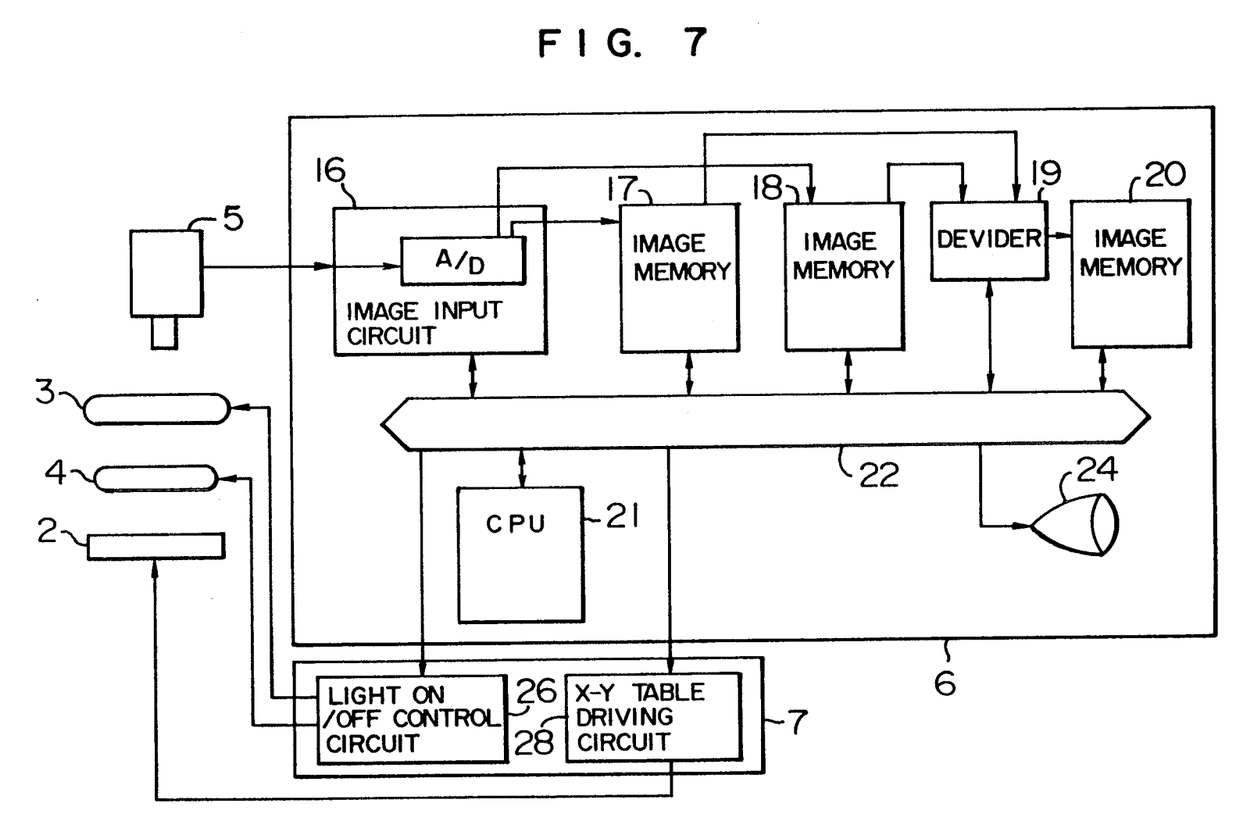
FIG. 7 is a block diagram showing an arrangement of the image processing unit and the control unit of FIG. 1.

FIG. 7 is a block diagram showing examples of the arrangement of the image processing unit 6 and the controller 7 shown in FIG. 1. A central processing unit (CPU) 21 includes a read only memory (ROM) and a random access memory (RAM). The operation of the arrangement in FIG. 7 will be described with reference to a flowchart of FIG. 8.

CPU 21 issues a positioning command through a bus 22 to an X-Y table driving circuit 28 in the controller. In response to this command, the driving circuit 28 gives a drive signal to the X-Y table 2 to drive the X-Y table to position a part under inspection right below the camera 5 (step 802).

Then, CPU 21 issues a lighting command through the bus 22 to a light on/off control circuit 26 to turn on either one of the lights 3, 4, the light 3, for example (step 804). In response to this command, the light on/off control circuit 26 supplies a lighting current to the light 3 to turn it on.

The CPU 21 issues a command to an image input circuit 16 to accept an image of a solder joint, illuminated by the light 3, which has been picked up by the camera 5. As a result, the image input circuit 16 accepts image data for one frame from the camera 5, and converts the image data into digital signals by a built-in analog-to-digital (A/D) converter. The CPU 21 issues a store command to an image memory 17, which accordingly stores image data for a frame in digital form (step 806). The CPU 21 issues an extinguishing command regarding the light 3 to the light on/off control circuit 26, which accordingly cuts off the lighting current to the light 3 to turn it off (step 808). The CPU 21 then issues a lighting command to turn on the light 4 to the light on/off control circuit 26 (step 810), and after the light 4 turns on, issues a command to store images made by illumination of the light 4 for forming a frame to the image input circuit 16. After accepting those images, the image input circuit 16 converts the image data into digital form, and in response to a command to store image data in the image memory 18, the image memory 18 stores the digital image data for forming a frame (step 812).

The CPU 21 issues an extinguishing command to the light on/off control circuit 26 to turn the light 4 off (step 814). Data stored in the image memories 17, 18 are values representing the brightness of the inspected area of the same object under inspection illuminated by the lights 3, 4.

The brightness values UPIC(I,J) and DPIC(I,J) at a pixel at the same position in the image are read out, are subjected to a division process by a divider 19 using Eq. (1) or (2) (step 816), and a resulting value DVDPIC(I,J) is stored in an image memory 20 (step 818). The process of steps 816 to 818 is performed for all pixels, where a division process needs to be executed, of images stored in the image memories 17, 18.

Data in the image memory 20 may be divided into a plurality of areas and may be displayed on a display device, a CRT 24, for example, by the gradation of brightness according to the division made as shown in FIGS. 4, 5, etc. (step 820).

As shown in FIG. 5D, it is possible to let the CPU 21 calculate the length L of the flat solder area from the end of the solder pad along the center line of the solder joint from data in the image memory 20 (a length or the number of pixels which conform to the range of (DVDPIC(I,J)≧(128+M)) where DVDPIC(I,J) derived from the division process corresponds to the displayed continuous white area in the X-direction from the right end of the window, for example), and judge the solder to be unacceptable if the length L is greater than a fixed value, and notify the judgment result by displaying on the CRT 24 or by sounding an alarm buzzer (not shown) (step 814).

Figure 9:
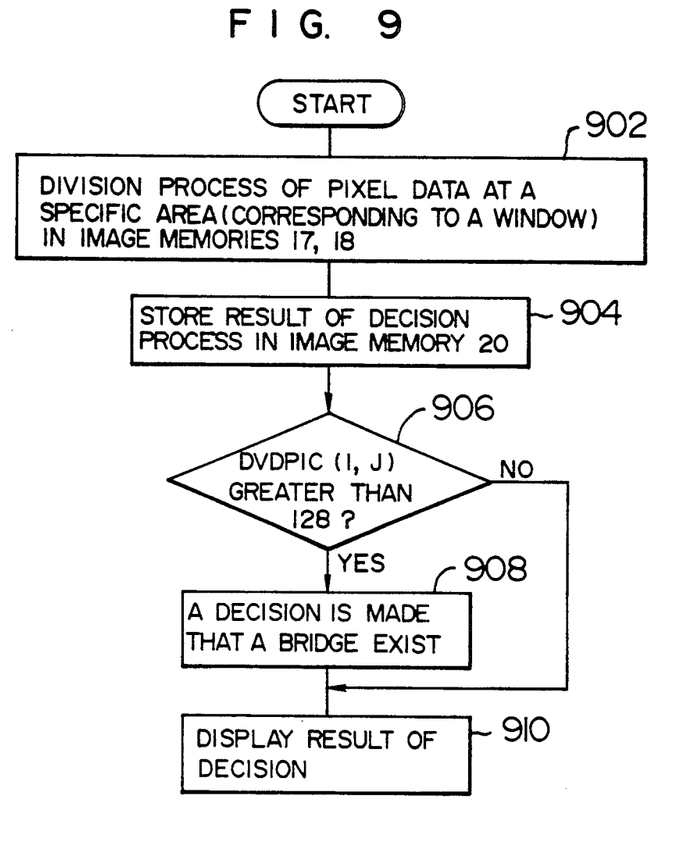
FIG. 9 is a flowchart for explaining the decision process about a bridge.

FIG. 9 is a flowchart showing a decision process about a bridge shown in FIG. 6C. Data at the same pixel in a specific image area (an area corresponding to the window 15 in FIG. 6C) in the image memories 17, 18 is read out and subjected to a division process using Eq. (1) or (2) (step 902), and the process result DVDPIC(I,J) is stored in the image memory 20 (step 904). The division process is performed for data at all pixels and the results are stored in the image memory 20. A decision is made whether or not there is any DVDPIC(I,J) in the image memory 20 that is less than 128. If there is not, a decision that there is no bridge is made, and displayed on the CRT (steps 906, 910). If there is, a decision that there is a bridge is made (steps, 906, 908), and the decision result is displayed on the CRT (step 910).

Figure 8:
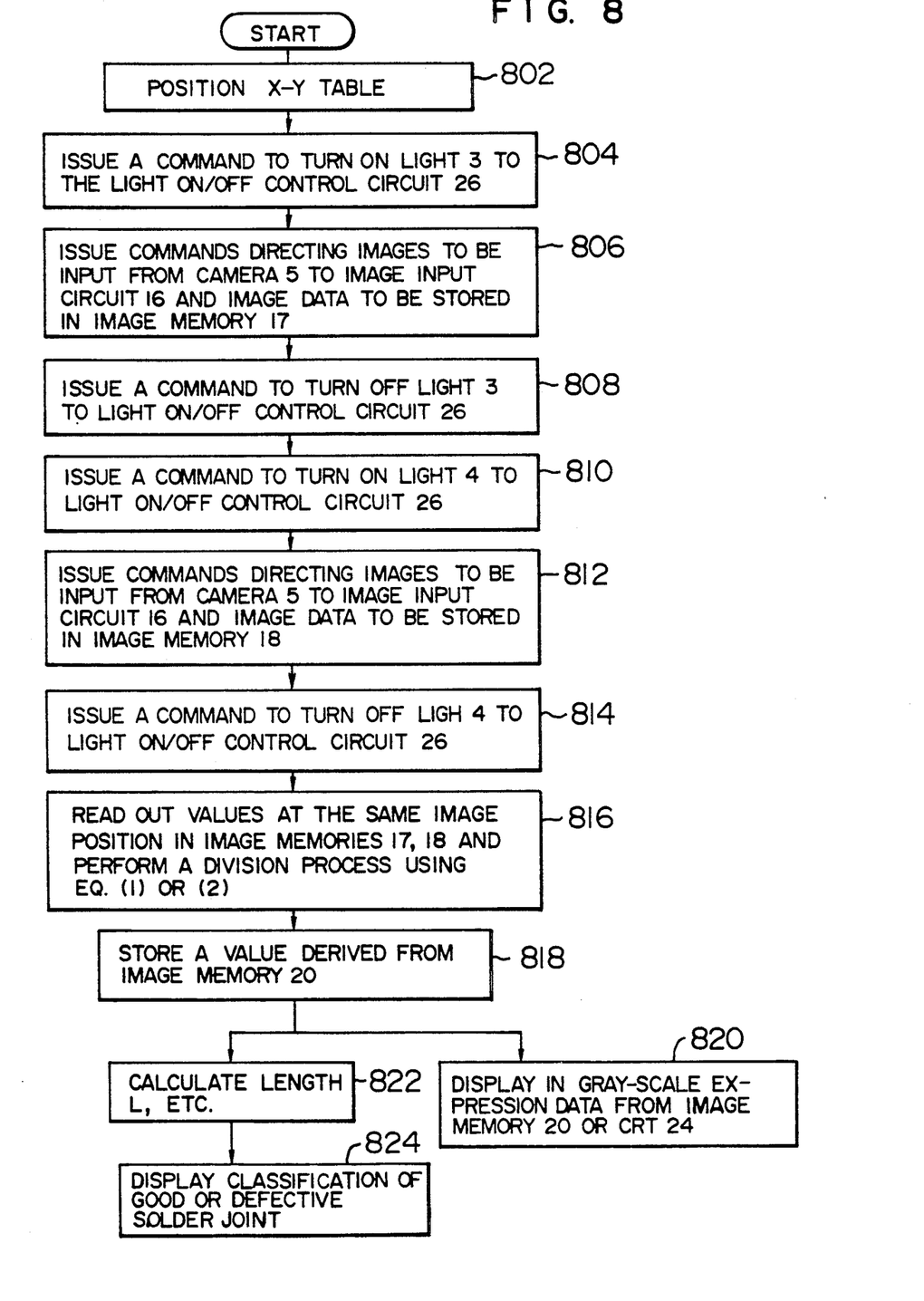
FIG. 8 is a flowchart for explaining the operation of the devices of FIG. 7.

FIGS. 8, 9 show examples of a decision process about the solder condition, and other decision processes may be used to make an accept-reject decision.

In FIG. 7, RAM in the CPU 21 may be used for the image memories 17, 18, and the division process in the divider 19 may be performed in the CPU 21.

Figure 10:
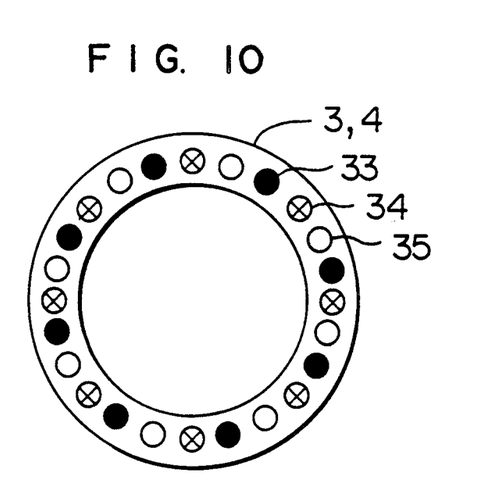
FIG. 10 is a bottom view showing an example of an illumination arrangement of FIG. 1.

FIG. 10 shows an example of the arrangement of the light 3 or 4 shown in FIG. 1 as seen from below. To input images by the upper and lower lights at high speed, it is necessary to perform switching of the lights at high speed. So, as shown in FIG. 10, a plurality of circular luminous elements, light-emitting diodes (LED) for example, are arranged. If LED lamps of the same wavelength are used, there is no problem so long as solder joints are inspected. However, in inspection of electronic parts or polarity markers, inspection will, in some cases, become difficult owing to the relation between wavelengths of the marker color and the light source. To solve this problem, as shown in FIG. 10, LEDs with different wavelengths may be mixed to form a light. In FIG. 10, LED lamps 33 are near-red, LED lamps 34 are green, and LED lamps 35 are yellow, for example, and those lamps may be arranged regularly in a circle. By assorting LEDs of different wavelengths to form a light, it is possible to obtain a light having a wide range of wavelengths close to natural light, and perform high-speed switching.

Figure 11:
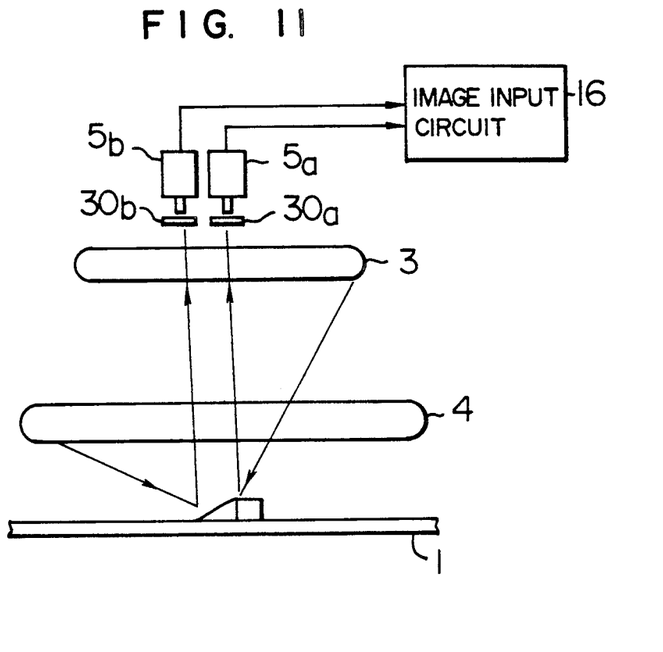
FIG. 11 shows an example of the optical system arrangement in another embodiment of this invention.

In the embodiment of FIG. 1, the upper and lower lights are switched over and images by the upper and lower lights are obtained alternately. However, it is possible to use upper and lower lights of different emission frequencies (or frequency bands), and obtain images by the upper and lower lights through two kinds of filter mounted in the camera. More specifically, as shown in FIG. 11, upper and lower lights 3, 4 of emission frequencies (frequency bands) $f_3$, $f_4$ are used, two cameras 5a and 5b are arranged close to each other, and filters 30a, 30b respectively allowing only frequencies $f_3$, $f_4$ to pass. Then, it is only necessary to give a command from the CPU 21 to the image input circuit 16 to accept images from the cameras 5a, 5b alternately.

Therefore, in this case, the lights 3, 4 may be formed respectively by combining LEDs of multiple emission frequencies.

Figure 12:
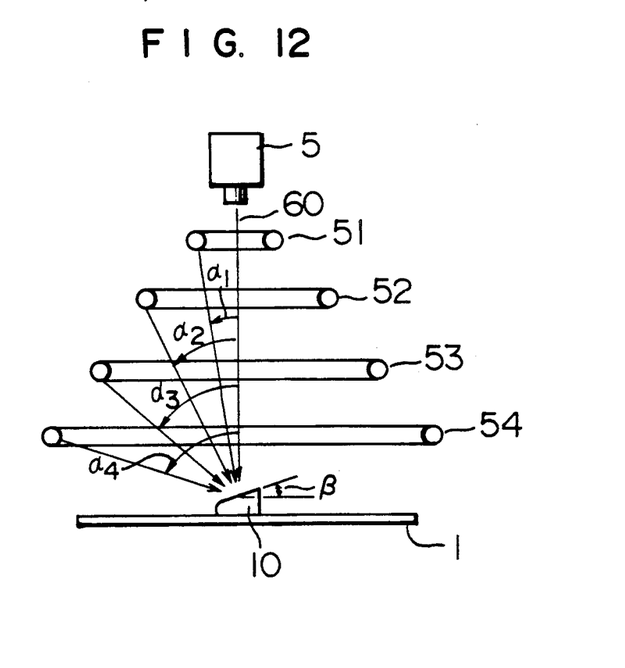
FIG. 12 shows an example of the optical system arrangement in still another embodiment of this invention.
Figure 13A:
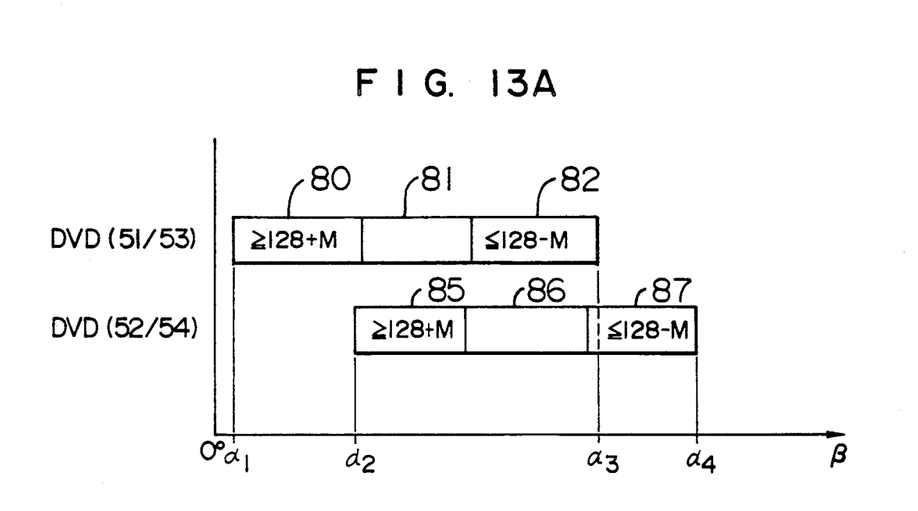
FIGS. 13A, 13B are diagrams showing the relation between the division-derived image values and the inclination of the surface of the object being inspected.

In the foregoing embodiments, the lights are provided in two stages, but they may be provided in three or more stages. An embodiment in such a case will be described with reference to FIGS. 12, 13. FIG. 12 shows an arrangement of the optical system in this embodiment. Ring lights 51 to 54 are provided in four stages, and the lights are arranged coaxially with respect to a line 60 connecting between the camera 5 and the object 10 being inspected. The inclinations formed by the lights 51 to 54 and the object 10 are denoted by $\alpha 1$, $\alpha 2$, $\alpha 3$, and $\alpha 4$. By alternately turning on and off the lights 51, 53, a division-derived image value DVDPIC-(I,J) at a pixel point (I,J) is calculated by using Eq. (1) or (2) mentioned above using the same method as in the embodiment described above. Here, this division-derived image value is represented by DVD(51/53). If the division-derived image values are classified into three ranges: more than $(128+M)$, less than $(128-M)$ and a range between $(128+M)$ and $(128-M)$ as in the foregoing embodiments, the relation between the inclination $\beta$ of the surface of the object 10 with respect to the board surface 1 and the division-derived image value is shown in FIG. 3A. In FIG. 3A, the ranges 80, 81, 82 are a range where DVD(51/53) is more than $128+M$, a range where DVD(51/53) is between $128+M$ and $128-M$, and a range where DVD(51/53) is less than $128-M$. Therefore, the inclination $\beta$ can be measured from the minimum $\alpha 1$ to the maximum $\alpha 3$.

Likewise, by turning on the lights 52, 54, the division-derived image value DVDPIC(I,J) (here expressed as DVD(52/54) at a pixel point (I,J) is calculated by using Eq. (1) or (2). If division-derived image values are classified into three ranges as in the above-mentioned embodiments, the ranges 85, 86, 87 are a range where DVD(52/54) is more than $128+M$, a range where DVD(52/54) is between $128+M$ and $128-M$, and a range where DVD(52/54) is less than $128-M$, and therefore, the inclination $\beta$ can be $\alpha 2$ to $\alpha 4$.

Figure 13B:
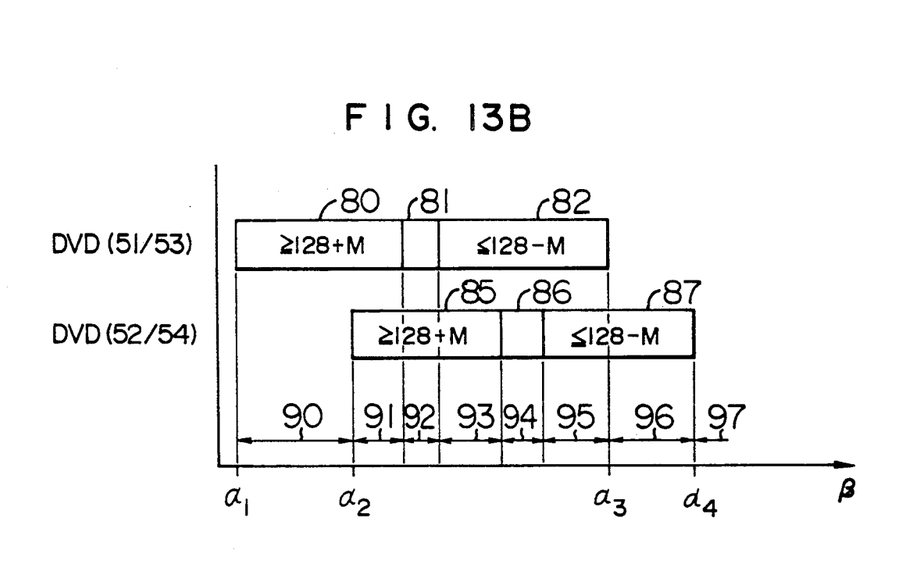

If a small value is used for the value of M, the ranges are set according to the values of DVD(51/53) and DVD(52/54) as shown in FIG. 13B. Therefore, it is possible to easily understand to which of the eight ranges 90 to 97 the inclination $\beta$ at the pixel point (I,J) belongs. For example, if the value of DVD(51/53) at a pixel point (I,J) belongs to the range 82 and the value of DVD(52/54) at the same pixel point belongs to the range 85, it is found that the inclination $\beta$ belongs to the range 93. In a gray-scale display over the ranges 90 to 97, if the range 90 is expressed in white, the range 97 is expressed in black representing an inclination steeper than $\alpha 4$ and the ranges from 91 to 96 are expressed in dark gray, gray-scale display can be made for each pixel point according to the degree of the inclination $\beta$.

For combinations of lights for a division process, combinations of lights 51, 52 or 53, 54 other than those mentioned above may be used.

According to the embodiments mentioned above, the degree of the inclination of the solder surface can be expressed on an image based on gray-scale values. This method makes it possible to inspect the shape of the solder joints without being affected by the frosty or contaminated appearance of the solder surface. In addition, this method enables solder joint inspection to be automated, so that the required labor can be reduced in the soldering process.

The apparatus according this invention is capable of not only inspecting the degree of the inclination, namely, the three-dimensional shape and pattern of the solder surface but also can be easily applied to inspection of the three-dimensional shape and pattern of other objects.

In this invention, the division-derived image values are displayed by gray-scale expression, but may be displayed in different colors.

What is claimed is:

1. An apparatus for inspecting a surface shape and pattern of an object, comprising:

first and second lighting means, provided on an inspected surface side of the object and provided at different heights from the object, for illuminating the inspected surface side of the object by emitting light;

imaging means for receiving images of the inspected surface side by the light reflected from the inspected surface side of the object illuminated by the first and second lighting means;

input means for storing a first image data from the images of the inspected surface side of the object illuminated by the first lighting means and storing a second image data from the images of the inspected surface side of the object illuminated by the second lighting means, said first image and second image being received from said imaging means; and division process means for calculating a ratio of said first image data and said second image data, to obtain a two-dimensional inclination signal corresponding to a inclination of the inspected surface side of the object and forming third image data from said two-dimensional inclination-signal, inspection means for generating windows corresponding to portions of said inspected surface side of the object and for processing said third image data to generate at least a two-dimensional flat area signal or a two-dimensional inclined area signal for each of said windows, said inspection means judging if each of the portions are flat or inclined in response to said two-dimensional flat area signal or said two-dimensional inclined area signal.

2. An apparatus according to claim 1, wherein each of said first and second lighting means comprises means for emitting said light having multiple wavelengths.

3. An apparatus according to claim 1, wherein said division process means comprises means for obtaining the two-dimensional inclination signal for each pixel of said third image data formed by said dimension process means, and for assigning different colors corresponding to the two-dimensional inclination signal to each pixel of said third image and displaying each pixel of said third image in a color according to the two-dimensional inclination signal at the pixel.

4. An apparatus according to claim 1, wherein said first lighting means and second lighting means comprise a first light and a second light, respectively, and said apparatus further includes light on/off control means for turning on and off said first light and said second light alternately, and wherein said input means comprises means for alternately storing the first image data and second image data received by said imaging means in synchronism with the turning on and off of said first light and said second light by said light on/off control means.

5. An apparatus according to claim 1, wherein a first frequency band of the light of said first lighting means are different than a second frequency band of the light of the second lighting means, and wherein said imaging means includes image pick-up means for separately receiving the reflected light of said first frequency band and second frequency band.

6. An apparatus according to claim 1, wherein said apparatus is adapted to inspect the condition of solder joints of parts mounted on a printed circuit board.

7. A method of inspecting a surface shape and pattern on a surface of an object, comprising the steps of:

providing first and second lighting means for emitting light on an inspected surface side of an object, said first and second lighting means being provided at different heights from the object for illuminating the surface of the object;

receiving images of reflected light rays from the inspected surface side of the object illuminated by said first and second lighting means;

separately inputting first image data of the inspected surface side of the object illuminated by the first lighting means and second image data of the inspected surface side of the object illuminated by the second lighting means;

forming third image data by calculating a ratio of said first image data and said second image data, to obtain a two-dimensional inclination signal corresponding to an inclination of the inspected surface side of the object; and processing said two-dimensional inclination signal to generate at least a two-dimensional flat area signal or a two-dimensional inclined area signal.

8. A method according to claim 7, further comprising the step of emitting light, said light having multiple wavelengths from the first and second lighting means.

9. A method according to claim 7, further comprising the steps of obtaining the two-dimensional inclination signal for each pixel of said third image data formed by the step of forming said third image and assigning different colors to each pixel of said third image based on the two-dimensional inclination signal.

10. A method according to claim 7, further comprising the steps of alternately turning on and off a first light of the first lighting means and a second light of the second lighting means and alternately inputting the first image data and second image data.

11. A method according to claim 7, further comprising the step of separating the first light into a first frequency band and the second light into a second frequency band, wherein said image receiving step comprises a step of separately receiving images of the reflected lights corresponding to said first frequency band and said second frequency band.

12. A method according to claim 7, wherein said object includes solder joints of parts mounted on a printed circuit board.

13. An apparatus for inspecting soldering, comprising:

an XY table for positioning an object to be inspected, said object being a printed circuit board having an electronic part soldered thereon;

a plurality of circular illuminating means for respectively illuminating a solder joint in substantially circular shapes, said plurality of circular illuminating means having respectively different inclination angles with respect to a surface of said printed circuit board;

imaging means for receiving images from reflected light rays from a surface of the solder joint being illuminated individually by said plurality of circular illuminating means, and for outputting a plurality of two-dimensional gray scale image signals, said imaging means receiving said images individually from a direction substantially perpendicular to the surface of said printed circuit board;

an image memory for storing the two-dimensional gray scale image signals being supplied individually from said imaging means;

division processing means for calculating a ratio from the two-dimensional gray scale image signals to obtain a two-dimensional inclination image signal corresponding to an inclination of the surface of the solder joint without being affected by a reflectivity of the surface of the solder joint; and inspection means for generating windows corresponding to portions of an inspected side of the object and for processing said two-dimensional inclination signal to generate at least a two-dimensional flat area signal or a two-dimensional inclined area signal for each of said windows; said inspection means judging if each of the portions are flat or inclined in response to said two-dimensional flat signal or said two-dimensional inclined signal.

14. An apparatus according to claim 13, further comprising
switching means for switching between said plurality of circular illuminating means to obtain each of the two-dimensional gray scale image signals individually from said imaging means.

15. An apparatus according to claim 13, wherein said circular illuminating means emit illuminating light rays having different frequencies, and said imaging means detecting each of the reflected light rays of the different frequencies separately so that each of the two-dimensional gray scale image signals are outputted separately.

16. An apparatus according to claim 15, wherein said imaging means include a plurality of imaging devices respectively corresponding to each of the different frequencies.

17. An apparatus according to claim 13, wherein each of said circular illuminating means emits an illuminating light ray having a plurality of wavelengths.

18. An apparatus according to claim 13, wherein said inspection means inspects by comparing each of the two-dimensional flat area signal and the two-dimensional inclined area with an inspection criterion.

* * * * *